US00PP34679P2

(12) United States Plant Patent
Gómez Porras et al.

(10) Patent No.: US PP34,679 P2
(45) Date of Patent: Oct. 25, 2022

(54) OLIVE TREE NAMED 'I-50'

(50) Latin Name: ***Olea europaea* L.**
Varietal Denomination: 'I-50'

(71) Applicant: Todolivo S.L., Cordova (ES)

(72) Inventors: Jose María Gómez Porras, Cordova (ES); Luis Rallo Romero, Cordova (ES); Diego Barranco Navero, Cordova (ES); Concepción Muñoz Díez, Cordova (ES); Carlos Trapero Ramírez, Cordova (ES); Pedro Valverde Caballero, Cordova (ES)

(73) Assignee: TODOLIVO, S.L., Cordova (ES)

( * ) Notice: Subject to any disclaimer, the term of this patent is extended or adjusted under 35 U.S.C. 154(b) by 0 days.

(21) Appl. No.: 17/376,634

(22) Filed: Jul. 15, 2021

(51) Int. Cl.
*A01H 5/08* (2018.01)
*A01H 6/00* (2018.01)

(52) U.S. Cl.
USPC ..... Plt./158

(58) Field of Classification Search
USPC ..... Plt./158
CPC ... A01H 5/08; A01H 5/02; A01H 5/00; A01H 5/04; A01H 5/10; A01H 6/00
See application file for complete search history.

(56) References Cited

U.S. PATENT DOCUMENTS

PP30,208 P2 * 2/2019 Cunill ..... A01H 5/08 Plt./158
PP32,302 P3 * 10/2020 Romero ..... A01H 6/00 Plt./158

OTHER PUBLICATIONS

Upov Pluto Plant Variety Database 20210923, retrieved on Sep. 27, 2021, retrieved from the Internet at https://www.upov.int/pluto/en/index.jsp, one page. (Year: 2021).*

* cited by examiner

*Primary Examiner* — June Hwu
(74) *Attorney, Agent, or Firm* — Buchanan Ingersoll & Rooney P.C.

(57) ABSTRACT

A new and distinct variety of olive tree, herein referred to by its cultivar name, 'I-50', is provided which forms a spreading growth habit. Fruit with a low weight and obtuse shape is produced. The fruit exhibit black coloration and the fruit nipple is either absent or weakly present. The stone of the fruit of the new variety is of very low to low weight, very elongated and possess a weakly rugose surface.

5 Drawing Sheets

Figure 1:
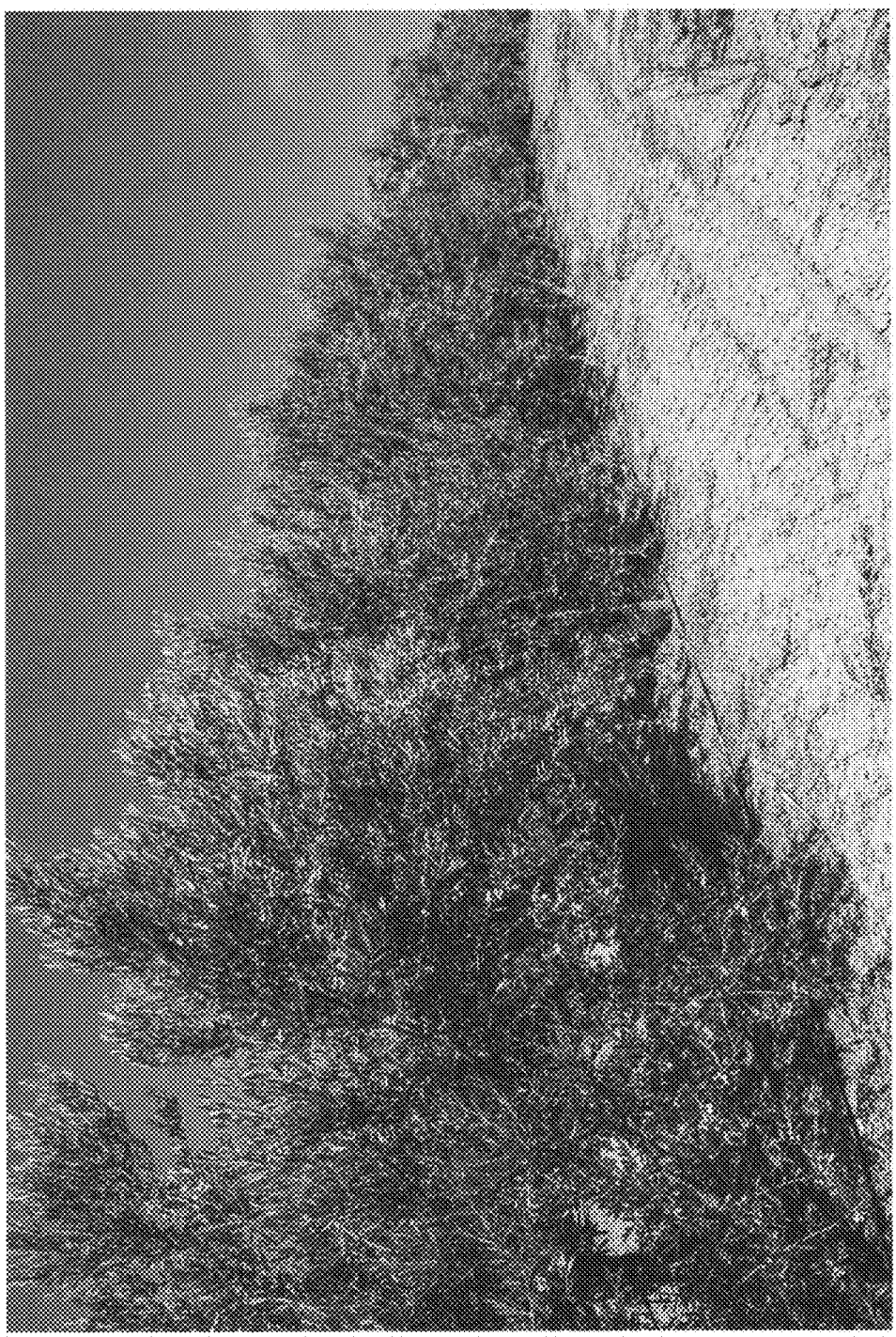

Botanical/commercial classification: Latin name: *Olea europaea* L. Common name: Olive tree.
Varietal Denomination: 'I-50'.

SUMMARY OF THE INVENTION

The new variety of olive tree of the present invention was created by a controlled cross in Spain wherein two parents which previously had been studied were crossed in the hope that they would contribute the desired characteristics. The female parent (i.e., seed parent) of the new variety was the 'ARBOSANA' variety (unpatented). The male parent (i.e., pollen parent) was the 'KORONEIKI' variety (unpatented).
The parentage can be summarized as follows:

'ARBOSANA' x 'KORONEIKI'.

The seeds resulting from the above pollination were sown and small plants were obtained which were physically and biologically different from each other. Selective study resulted in the identification of a single plant of the new variety.

The new variety's color is a less intense green when compared to the color of the 'Arbosana' variety. The new variety has a higher yield fat than 'Arbosana'. The new variety's size is smaller than the 'Koroneiki' variety and similar to 'Arbosana'. Table 1 further lists some of the differences and similarities between the new variety and its parentage.

TABLE 1

Differences and similarities between new variety and its parentage

| DIFFERENCES | I-50 | ARBOSANA | KORONEIKI |
|---|---|---|---|
| TREE TYPE | Normal | Semi-Dwarf | Normal |
| TREE HABIT | Spreading | Spreading | Spreading |
| FRUIT WEIGHT | About 1.6 g | About 1.43 g | About 1.07 g |
| STONE WEIGHT | About 0.2 g | About 0.23 g | About 0.19 g |

The new variety is different from the related 'I-15' variety (patented as U.S. Plant Pat. No. 32,302 P3) since it has an earlier bearing than 'I-15'. The new variety is also different from the 'I-30' variety (U.S. Ser. No. 17/376,725) since it has at least 3 points more oil yield (percentage of olive oil in fruit). Table 2 further lists some of the differences and similarities between the new variety and related cultivars, such as the 'I-42' variety (U.S. Ser. No. 17/376,586).

TABLE 2

Differences and similarities between new variety and related cultivars

| DIFFERENCES | I-42 | I-50 | I-30 | I-15 |
|---|---|---|---|---|
| TREE TYPE | Semi-Dwarf | Normal | Semi-Dwarf | Normal |
| TREE HABIT | Spreading to dropping | Spreading | Spreading to dropping | Spreading |
| RIPENESS | Early | Early | Early | Medium |
| LEAF LENGTH | About 62 mm | About 50 mm | About 56 mm | About 52 mm |
| MAXIMUM FRUIT DIAMETER (Transversal) | About 12 mm | About 15 mm | About 15 mm | About 15 mm |

It was found that the new variety of the present invention possesses the following combination of characteristics:

(a) the tree has a spreading growth habit
(b) the fruit weight is low and the fruit color is black
(c) the fruit is obtuse and weakly asymmetric
(d) the fruit possesses either an absent or weak nipple
(e) the stone is very elongated with a very low to low weight and possesses a weakly rugose surface.

The new variety well meets the needs of the horticultural industry and has not been commercialized. The new variety has an easy agronomic management.

The new variety can be readily distinguished from related similar varieties. The new variety has a small variety size.

The new variety has been found to undergo asexual propagation in Villafranca de Córdoba, Córdoba, Spain by vegetative cuttings. Asexual propagation by vegetative cutting in Spain has shown that the characteristics of the new variety are stable and are strictly transmissible by such asexual propagation from one generation to another. Accordingly, the new variety undergoes asexual propagation in a true-to-type manner.

The new variety has been named 'I-50'.

BRIEF DESCRIPTION OF THE PHOTOGRAPHS

The accompanying photographs show as nearly true as it is reasonably possible to make the same, in a color illustration of this character, typical specimens of the plant parts of the new variety.

Figure 2:
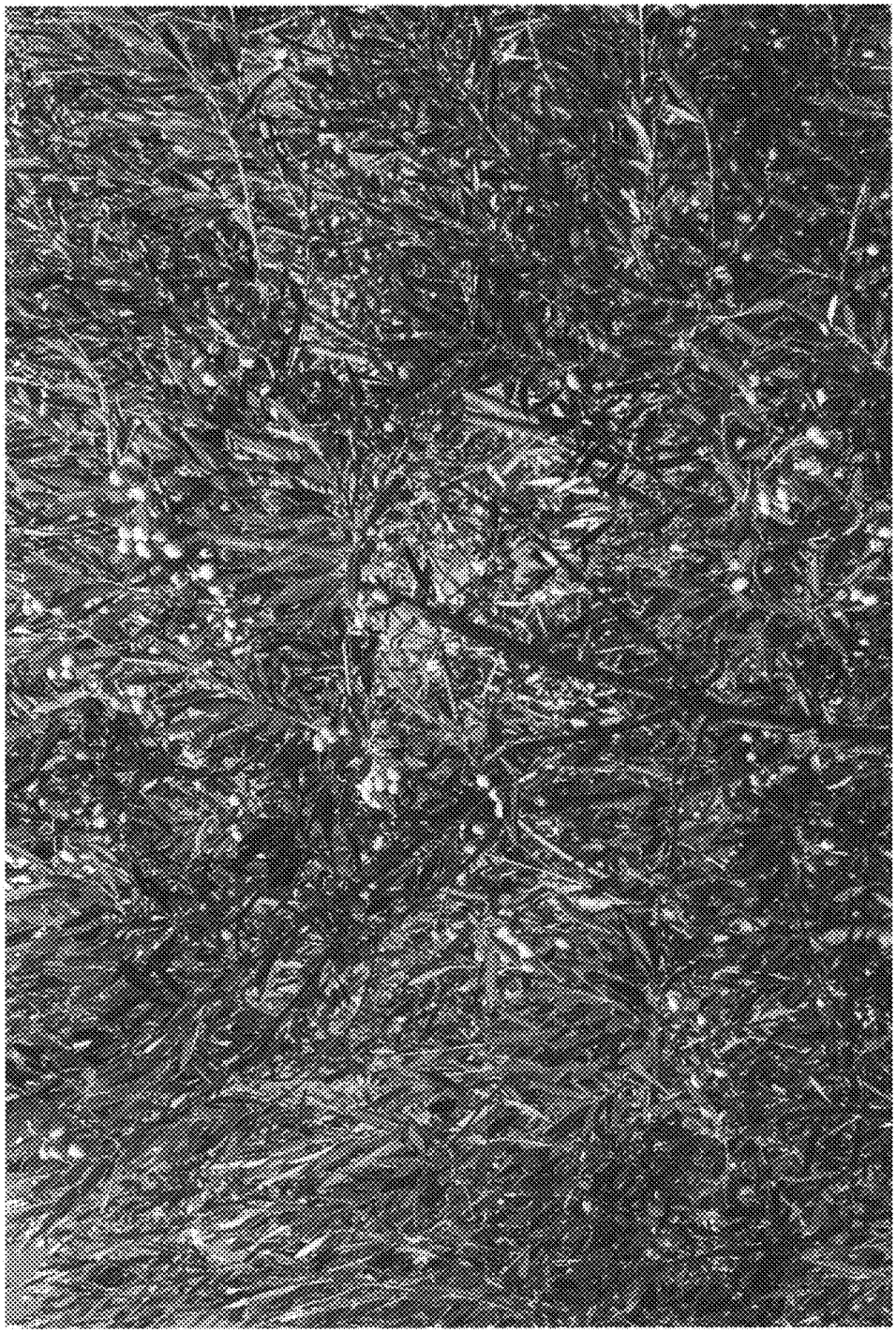
Figure 3:
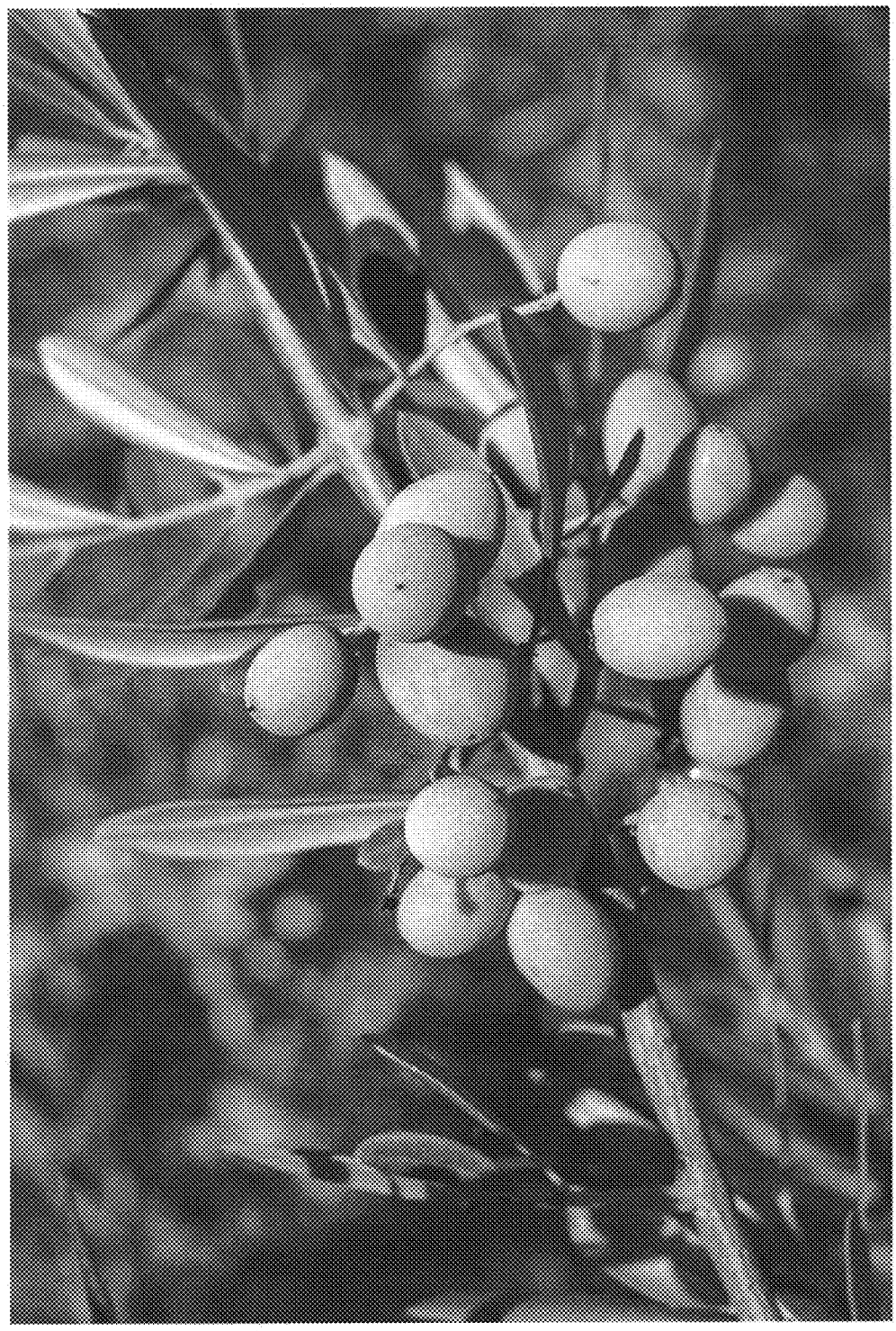
Figure 4:
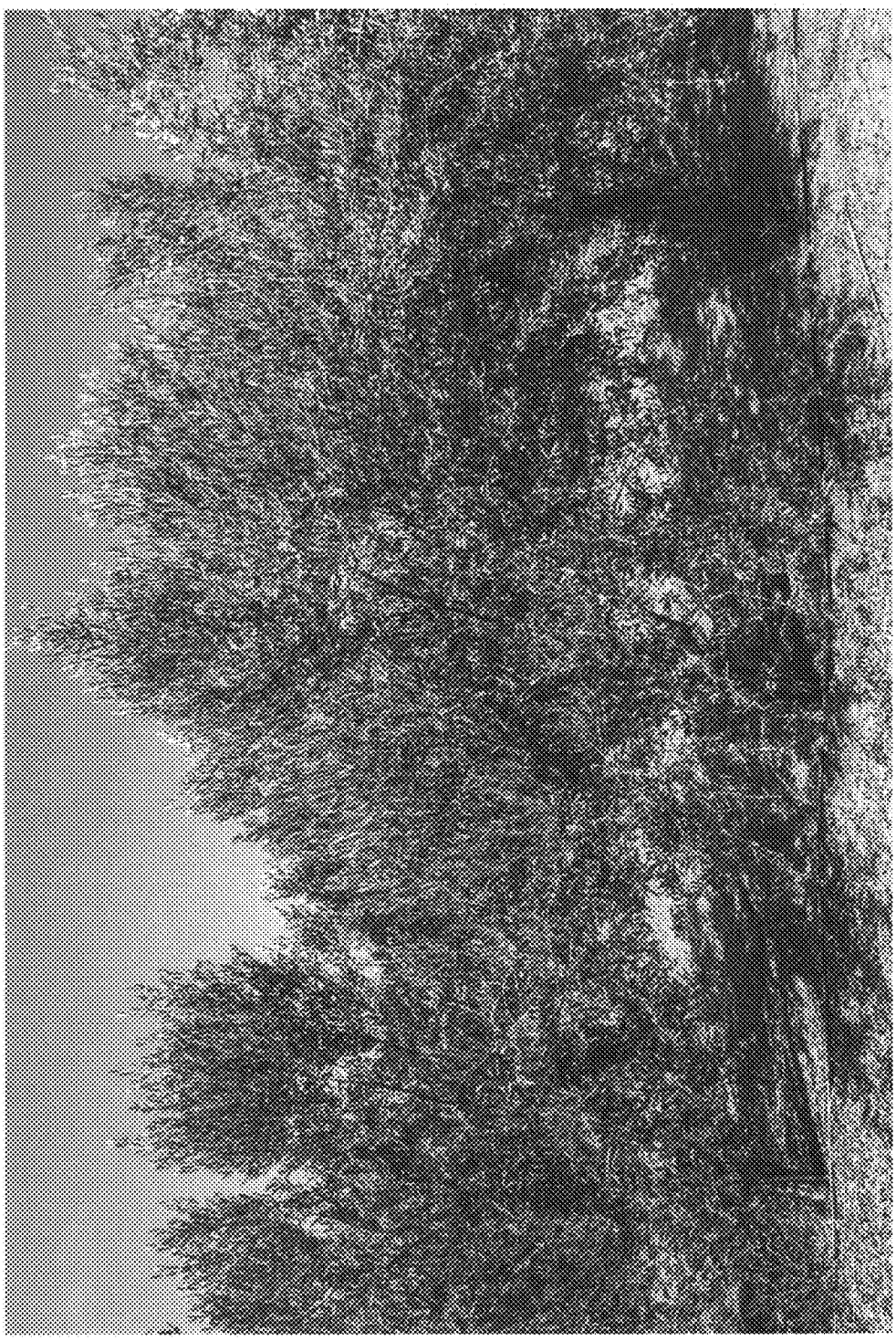
Figure 5:
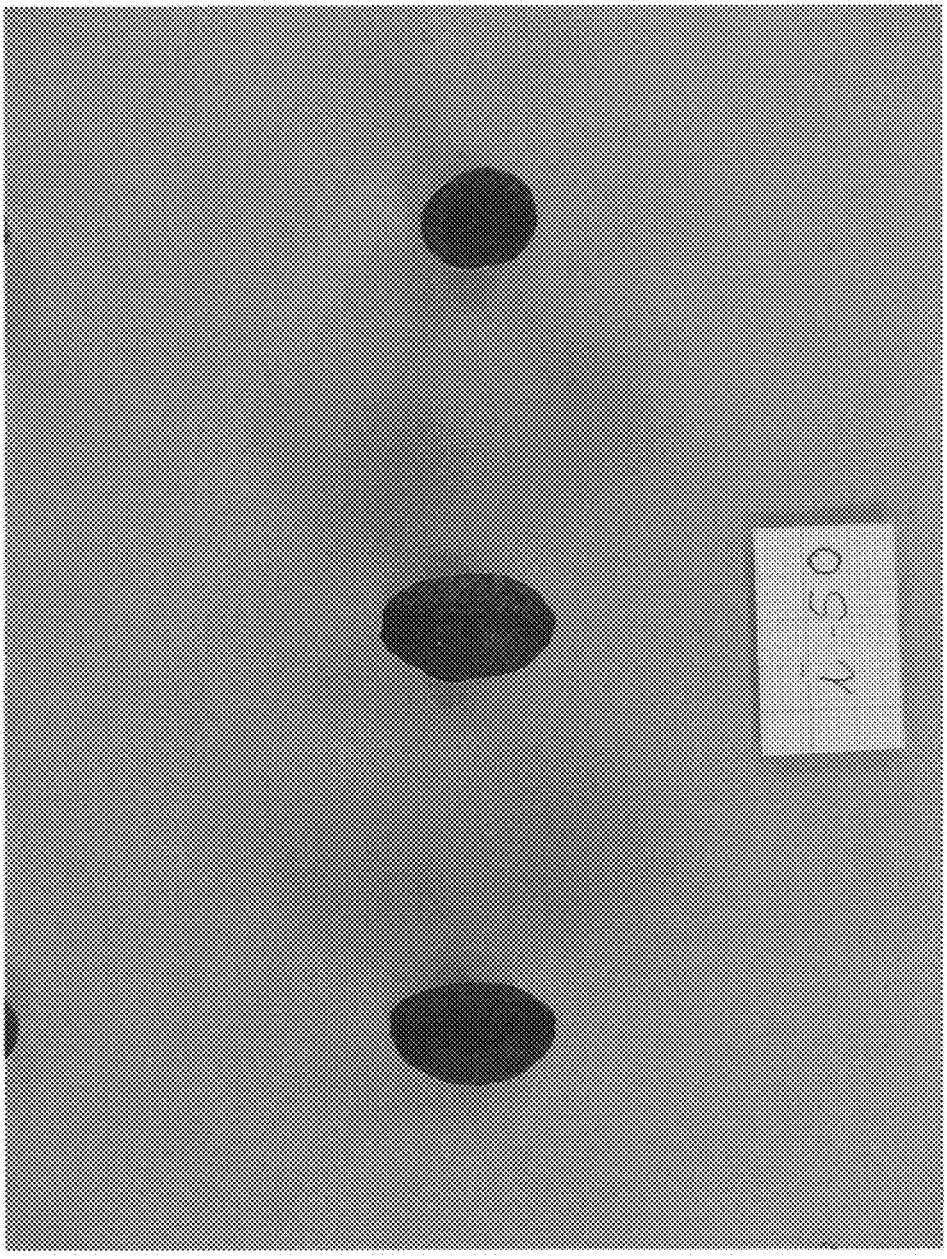

FIG. 1—illustrates the growth of the new variety.
FIG. 2—illustrates the foliage of the new variety.
FIG. 3—illustrates specimens of the new variety's immature fruit.
FIG. 4—illustrates the growth habit of the new variety.
FIG. 5—illustrates the new variety's mature fruit.

DETAILED BOTANICAL DESCRIPTION

The chart used in the identification of the colors is that of The Royal Horticultural Society (R.H.S. Colour Chart, 2007 edition), London, England. The terminology which precedes reference to the chart has been added to indicate the corresponding color in more common terms. The description is based on data collected from a four-year-old specimen during 2019 in Villafranca (Córdoba, Spain).

Plant:
- *Growth habit.*—Spreading.
- *Vigor.*—Medium.
- *Height* (*average*).—220 cm.
- *Width* (*average*).—160 cm.
- *Canopy width.*—160 cm.
- *Canopy density.*—Dense.
- *Branching habit.*—Spreading-drooping.
- *Growth period.*—All year, less in winter or stronger in summers.

Trunk:
- *Surface texture.*—Smooth.
- *Bark color.*—148C (greyish yellow green).
- *Diameter.*—47 mm (measured at a height of 50 cm).
- *Cross-section.*—47 mm (diameter).

Main stems:
- *Length* (*average*).—220 cm.
- *Amount of main branches.*—5.
- *Circumference* (*average*).—47 mm.
- *Color designation* (*young stems*).—148C (greyish yellow green).
- *Color designation* (*mature stems*).—148A (moderate yellow green).
- *Surface texture* (*young stems*).—Smooth.
- *Surface texture* (*mature stems*).—Smooth.
- *Lenticels.*—Medium.
- *Internode length* (*average*).—10-20 mm.
- *Cross-section.*—59 mm.

Lateral branches:
- *Abundance.*—High.
- *Cross-section.*—15-25 cm.
- *Average.*—Length 85 cm.
- *Diameter* (*average*).—25 cm.
- *Internode length* (*average*).—15 cm.
- *Texture.*—Smooth.
- *Strength.*—Medium.
- *Color designation* (*young branches*).—148C (greyish yellow green).
- *Color designation* (*mature branches*).—148A (moderate yellow green).
- *Fruiting shoots.*—All.
- *Pubescence.*—Absent.

Leaves:
- *Arrangement.*—The arrangement of the leaves is typical of *Olea europaea* L. Species (two opposite leaves per each node).
- *Venation pattern.*—Central line.
- *Length* (*average*).—50 mm.
- *Width* (*average*).—10 mm.
- *Color* (*upper surface*) *young leaves.*—142A (light green).
- *Color* (*lower surface*) *young leaves.*—142D (light green).
- *Color* (*upper surface*) *mature leaves.*—143A (medium green).
- *Color* (*lower surface*) *mature leaves.*—142D (light green).
- *Leaf margins.*—Smooth.
- *Texture.*—Smooth (Both upper and lower surfaces).
- *Shape.*—Elongated.
- *Curvature of longitudinal axis.*—None.

Petiole:
- *Average length.*—4-6 mm.
- *Average diameter.*—1 mm.
- *Color.*—148C (greyish yellow green).

Inflorescence:
- *Type.*—Raceme.
- *Average length.*—Medium.
- *Average width.*—Medium.
- *Number of flowers* (*average*).—At least 15.
- *Flower bud size.*—Medium.
- *Flower bud shape.*—Medium.

*Flower bud color.*—142D (light green).
*Flowering time.*—First of May in Villafranca de Córdoba (Córdoba, Spain) during 2 weeks.

Peduncle:
*Average length.*—3 mm.
*Average diameter.*—1 mm.
*Texture.*—Smooth.
*Strength.*—Medium.

Flower:
*Type.*—In raceme.
*Shape.*—Ovate.
*Diameter* (*average*).—6 mm.
*Height* (*average*).—5 mm.
*Sepals.*—4 sepals in cross (unfused).
*Sepal length* (*average*).—3 mm.
*Sepal width* (*average*).—2 mm.
*Sepal shape.*—Elongated.
*Sepal apex shape.*—Peak.
*Sepal base shape.*—Rounded.
*Sepal margin.*—Smooth.
*Sepal texture.*—Smooth.

Androecium:
*Stamen number.*—2.
*Filament length.*—3 mm.
*Anther attachment.*—Basifixed.
*Anther shape.*—Globular (monothecal).
*Anther length.*—2 mm.
*Pollen amount.*—*Unknown.*

Gynoecium:
*Pistil quantity.*—1.
*Stigma shape.*—Ovate.
*Stigma length.*—2 mm.
*Style length.*—2 mm.
*Ovary position.*—Superior.
*Ovary shape.*—Hypoginus.
*Ovary diameter.*—About 2 mm.
*Carpels.*—1.

Calyx:
*Number* (*average*).—4.
*Shape.*—In cross shape.
*Base.*—Fused.
*Margin.*—Smooth.
*Texture.*—Smooth.
*Color* (*upper*).—155A (White).
*Color* (*lower*).—155A (White).

Pedicel:
*Length* (*average*).—1-5 mm.
*Diameter* (*average*).—1 mm.
*Color.*—145D (light green).
*Texture.*—Smooth.

Fruit:
*Average weight.*—1.6 g (low).
*Shape-apex.*—Obtuse.
*Color designation* (*flesh color*).—59A (dark purple red).
*Color designation* (*skin color*).—58C (medium purple red); as the fruit matures, the color changes from a 202A (black) to the 58C (medium purple red).
*Ripening.*—Intermediate.
*Fat yield.*—26%.
*Size* (*average*).—Small.
*Length* (*average*).—18 mm.
*Width* (*average*).—14 mm.
*Height* (*average*).—18 mm.
*Marbling.*—Medium.
*Symmetry.*—Symmetric.
*Pistil scar.*—Central.
*Mucron.*—Absent.
*Lenticel size* (*immature fruit*).—Medium.
*Number of lenticels* (*immature fruit*).—Medium.
*Nipple.*—Absent.
*Fruit bloom intensity.*—Medium.

Stalk:
*Length* (*average*).—5 mm.
*Diameter* (*average*).—1 mm.
*Color.*—148C (greyish yellow green).

Stone:
*Qantity.*—1.
*Shape.*—Very elongated.
*Average weight.*—0.20 g (very low to low).
*Average length.*—10 mm.
*Average width.*—5 mm.
*Grooving.*—7.
*Sutures.*—Medium.
*Color.*—152C (medium green brown).
*Symmetry.*—Symmetrical.
*Texture.*—Weakly rugose.
*Mucron.*—Present.

Development:
*Productivity.*—Very high and constant, 764 oil liter per acre a year, with approximately 800 trees per acre.
*Time of flowering.*—First days of may in Villafranca de Córdoba, Spain.
*Flowering period.*—2 weeks.
*Time of fruit ripening.*—3 months.
*Ripening period.*—October-December.
*Winter hardiness/cold tolerance.*—Unknown.
*Drought/heat tolerance.*—Unknown.
*Plant/fruit disease, pest resistance.*—Free of Cucumovirus cucumber mosaic virus (CMV), Nepovirus cherry leaf roll virus (CLRV), Incertae Sedis strawberry latent ringspot virus (SLRSV) and Nepovirus *Arabis* mosaic virus (ArMV).
*Fruit usage.*—High quality shipping in proper conditions. Long storage life of the fruit in suitable conditions. Main use for the production of extra virgin olive oil.

The new 'I-50' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of olive tree named 'I-50', as illustrated and described herein.

* * * * *